US008173070B2

(12) United States Patent
Gerhardt et al.

(10) Patent No.: US 8,173,070 B2
(45) Date of Patent: May 8, 2012

(54) SAMPLE INJECTOR SYSTEM FOR LIQUID CHROMATOGRAPHY

(75) Inventors: Geoff C. Gerhardt, Millbury, MA (US); James W. Jorgenson, Chapel Hill, NC (US); Keith Fadgen, Hope Valley, RI (US)

(73) Assignee: Waters Technologies Corporation, Milford, MA (US)

( * ) Notice: Subject to any disclaimer, the term of this patent is extended or adjusted under 35 U.S.C. 154(b) by 997 days.

(21) Appl. No.: 10/586,114

(22) PCT Filed: Jan. 18, 2005

(86) PCT No.: PCT/US2005/002401
§ 371 (c)(1),
(2), (4) Date: Aug. 24, 2007

(87) PCT Pub. No.: WO2005/071396
PCT Pub. Date: Aug. 4, 2005

(65) Prior Publication Data
US 2007/0283746 A1 Dec. 13, 2007

Related U.S. Application Data

(60) Provisional application No. 60/538,683, filed on Jan. 23, 2004.

(51) Int. Cl.
*G01N 30/16* (2006.01)
(52) U.S. Cl. ......... 422/70; 422/68.1; 422/500; 422/501; 422/509; 73/61.56; 73/61.57; 73/61.52; 436/180; 210/635; 210/656; 210/198.2

(58) Field of Classification Search .............. 73/61.52, 73/61.56; 436/180; 422/68.1, 70, 501–544, 422/99–104; 210/635, 656, 198.2
See application file for complete search history.

(56) References Cited

U.S. PATENT DOCUMENTS

| 3,186,234 A | 6/1965 | Solnick et al. |
| 3,621,263 A * | 11/1971 | Gilson et al. ............... 250/201.1 |
| 4,939,943 A | 7/1990 | Strohmeier |
| 5,672,810 A * | 9/1997 | Shibamoto ................ 73/23.25 |
| 5,795,788 A | 8/1998 | Bevan et al. |
| 6,148,680 A | 11/2000 | Baeuerle et al. |
| 6,159,744 A | 12/2000 | Bevan et al. |
| 6,190,550 B1 * | 2/2001 | Oberhauser ............... 210/198.2 |
| 6,290,909 B1 | 9/2001 | Paul et al. |

(Continued)

FOREIGN PATENT DOCUMENTS

| JP | 9033502 | 2/1997 |
| WO | 2004025153 | 3/2004 |

OTHER PUBLICATIONS

Bevan et al. "Use of Freeze-Thaw Flow Management for Controlling and Switching Fluid Flow in Capillary Tubes." Analytical Chem. 1995, 67, 1470-1473.*

(Continued)

*Primary Examiner* — In Suk Bullock
*Assistant Examiner* — Sharon Pregler
(74) *Attorney, Agent, or Firm* — Timothy M. Bryan

(57) ABSTRACT

An injection device (10) includes a carrier inlet (40), a sample inlet (46), waste outlet (44) and a chamber outlet (64) attached to separation column (66). Valves (52, 54, 56) are used to control flow such that sample flows into chamber (22) and is carried into the chamber outlet (42).

54 Claims, 9 Drawing Sheets

U.S. PATENT DOCUMENTS 6,387,234 B1 * 5/2002 Yeung et al. .......... 204/451
6,557,575 B1 5/2003 Gerhardt et al.

OTHER PUBLICATIONS

Translation of Notice of Rejection for Japanese Patent Application No. 2006-551418, mailed Sep. 21, 2010, 2 pages.

United Kingdom Patent Application No. GB0615960.2, Examination Report, dated Jan. 23, 2007, 2 pages.
United Kingdom Patent Application No. GB0615960.2, Examination Report, dated Dec. 12, 2008, 3 pages.
United Kingdom Patent Application No. GB0615960.2, Examination Report, dated Apr. 8, 2009, 3 pages.

* cited by examiner $$\pi r_i^2 \cdot d \cdot \sim \; =$$

SAMPLE INJECTOR SYSTEM FOR LIQUID CHROMATOGRAPHY

CROSS REFERENCE TO RELATED APPLICATIONS

This application claims priority from U.S. Provisional Patent Application No. 60/538,683, filed Jan. 23, 2004. The contents of these applications are incorporated herein by reference.

STATEMENT ON FEDERALLY SPONSORED RESEARCH

N/A

FIELD OF THE INVENTION

The present invention is generally related to liquid chromatography and, more particularly, is directed to operating at high, very high and ultra high pressure for liquid chromatography.

BACKGROUND OF THE INVENTION

As used herein, the term "High Pressure Liquid Chromatography" (HPLC) means chromatography performed under pressures of up to 4,000 psi. There has been interest in performing liquid chromatography at elevated pressures, such as —Very High Pressure Liquid Chromatography (VH-PLC): 6,000-20,000 pounds per square inch (psi) and Ultra High Pressure Liquid Chromatography (UHPLC): 20,000-120,000 psi. At pressures greater than 6,000 psi, injection valves typically used in HPLC applications fail due to leakage.

When performing on-line operations with a liquid chromatography separation column, an apparatus needs to alternate between supplying solute and supplying sample to the column. Valves have been the primary means used to switch between the solute and the sample. One mechanism has been the rotary injector valve where solute is directed to the column for one position of the valve and solute is directed through a loop containing a sample for the other position of the valve, thus introducing the sample as a discrete plug in the flowing stream. This mechanism works well when the pressure needed to inject is less than 5,000 psi. However, the improved chromatographic resolution of columns packed with smaller diameter particles, which require higher pressures to move liquids through them, is moving the industry toward columns where an increased pressure is required. Hardening the valves associated with the rotary injector allows the rotary injector valve to operate at up to 15,000 psi, but there is excessive wear and the valves exhibit a shorter lifetime.

A method of using fluid within nano-scale capillaries and channels (Nano-scale capillaries and channels are those having an inner diameter less than 200µ) to act as an on/off valve by freezing and thawing that liquid is known in the art, see, for example, U.S. Pat. Nos. 6,159,744 and 5,795,788. It has been found that the flow of liquids can be stopped or diverted to a further channel or chamber by merely freezing and thawing the liquid contained within a nano-scale segment of tubing or channel. This flow-switching device, referred to as "freeze-thaw valving," requires no moving parts and most importantly contributes no dead volume within the analytical system. Freeze-thaw valving systems are essentially on/off fluidic valves that operate on the fused silica capillaries typically used for fluid connections and columns in liquid chromatography involving pressures greater than 4,000 psi. While activation times for these valves can be in the subsecond range, they close more slowly (5 sec typical) than they open. Further information about free-thaw valving may be reviewed in Applicant's U.S. PCT applications PCT/US/03/28910 and U.S. Pat. No. 6,557,575 each of which is hereby expressly incorporated by reference in their entirety.

A further means to load a sample onto a column is a manual process that uses a high pressure vessel dedicated to the loading purpose. One end of a HPLC column is placed in the chamber of this vessel at ambient pressure. The chamber is filled with the sample and then the vessel is brought to a high pressure, which forces a portion of the sample onto the top of the column. The high pressure is maintained for the length of time necessary to load a known quantity of sample onto the column. The pressure is returned to ambient after the loading operation and the loaded column is then removed from the loading vessel. The loaded column may be manually installed on a separation apparatus immediately or stored and undergo separation at a later time. In the separation apparatus, a high pressure pump is connected directly to the column and forces an elutant through the column and toward the detector device, such as a mass spectrometer. This sequence of operations must be repeated for each sample to be analyzed.

There is a need to have an apparatus that can, in an automated fashion, deposit a sample on a column and run the separation through the column at high pressures.

SUMMARY OF THE INVENTION

The present invention is directed to a device for impelling one or more fluids through a HPLC column. The device comprises a housing with a number of openings, conduits in the openings, and at least one valve means to control flow in the conduits. The HPLC column is connected to a conduit that exits from the device.

The housing has a chamber for receiving and/or holding one or more fluids under pressure and an exterior surface. The housing has at least a first exit opening, a first inlet opening, a second exit opening, and a second inlet opening. Each opening extends from the chamber to the exterior surface. Each opening can receive a conduit.

A first exit conduit means is received by the first exit opening. The first exit conduit means is in communication with the chamber for transporting fluids from the chamber out of the first exit opening. The first exit conduit means is used for connection with an analytical device, such as a HPLC column. The first inlet opening receives a first inlet conduit means. The first inlet conduit means is in communication the chamber for transporting a first fluid into the chamber. The first inlet conduit means is used for connection to a first supply device, such as a pump.

The second inlet opening receives the second inlet conduit means. The second inlet conduit means is in communication with the chamber for transporting a second fluid into the chamber. The second inlet conduit means is used for connection with a second supply device, such as a reservoir or pump. The second exit conduit means is received by the second exit opening. The second exit conduit means is in communication with the chamber for transporting fluids from the chamber out of the second exit opening. The second exit conduit means is used for connection with a waste receptacle or recycling means.

At least one valve means is disposed in at least one of the first exit conduit means, the second exit conduit means and the second inlet conduit means. Each of the at least one valve means is operable with a pressure differential across the valve means of up to 120,000 psi. Each valve means has a closed position wherein fluid is prevented from flowing through the valve means and an open position wherein the fluid is allowed to flow through the valve means, Each valve means is responsive to a signal to assume one of the positions. The chamber is therefore adapted for receiving fluid from each of the first inlet conduit means and the second inlet conduit means, and for discharging fluid through the first exit conduit means and the second exit conduit means. Preferably the first fluid is a solute while the second fluid is sample fluid.

In one embodiment, the at least one valve means is a freeze-thaw valve. In particular the embodiment has a first exit conduit valve means interposed in the first exit conduit means. The first exit conduit means may be a capillary having a first end in the first exit opening, a mid-portion external to the housing, and a second end formed as a liquid chromatography column having an input end and an output end. The first exit conduit valve means is disposed in the mid-portion of the first exit conduit means. In a further embodiment, the first end of the capillary extends into the chamber with the tip of the first end of the capillary positioned in the chamber between the second inlet opening and the second exit opening.

In one embodiment, a second exit conduit valve means is interposed in the second exit conduit means. Preferably, second inlet conduit valve means is interposed in the second inlet conduit means. A second fluid source can be connected to the second inlet conduit for supplying the second fluid. In one embodiment, the device also comprises a first supply device connected to the first inlet conduit means. The first supply device has a supply state wherein the first fluid is supplied at a pressure up to a maximum pressure. The first supply device also has a stop state wherein the first fluid is not supplied. The first supply device is responsive to a supply signal to assume one of the states.

In one embodiment, the device also comprises a control means for controlling each of the at least one valve means by sending a signal to the valve means to assume one of the open and closed positions. Preferably, the control means further controls the first supply device by sending a supply signal to the supply device to assume one of the supply and stop states.

In one embodiment, the control means sends a supply signal to the first supply device to effect a supply state of the first supply device. The control means further sends one or more signals to the at least one valve means to effect a closed position of all conduit valve means for filling and pressurizing the chamber. Further, the control means sends a supply signal to the first supply device to effect a stop state of the first supply device and send one or more signals to the at least one valve means to effect a closed position of the first exit conduit valve means and an open position of the second inlet conduit valve means and the second exit conduit means for replacing a fluid currently in the chamber with the second fluid. The device may comprise a fluid monitor for monitoring a fluid passing through the second exit conduit means. The fluid monitor is for providing the control means with information about the composition of the fluid exiting the chamber. The control means monitors the fluid at the second exit conduit and determines the concentration of second fluid.

Preferably, the control means sends a supply signal to the first supply device to effect a stop state of the first supply device and sends one or more signals to the at least one valve means to effect a closed position of the first exit valve means and the second inlet valve means and an open position of the second exit valve means for discharging fluid from the chamber. Further, the control means sends supply signal to the first supply device to effect a supply state of the first supply device and send one or more signals to the at least one valve means to effect a closed position of the second inlet valve means and the second exit valve means and an open position of the first exit valve means for impelling a pressurized fluid through the first exit conduit means.

In one embodiment, the chamber is designed and constructed to hold fluids at pressures between approximately atmosphere and the maximum pressure. In one embodiment the maximum pressure may extend to approximately 5000 psi. In another embodiment the maximum pressure may extend to approximately 15,000 psi. In a third embodiment the maximum pressure may extend to approximately 120,000 psi and in particular, the pressure in the chamber is between approximately 30,000 psi and 100,000 psi when fluid is impelled through the first exit opening.

Preferably, the embodiments further comprise a vent opening in the housing extending from the chamber to the exterior surface for receiving a vent conduit means. The vent conduit means that is received by the vent opening is in communication with the chamber for transporting fluids from the chamber out of the vent opening. The vent conduit means may be connected to a vent conduit valve means. The vent conduit valve means interposed in the vent conduit means has an open position wherein fluid is allowed to flow through the vent conduit valve means and a closed position wherein fluid is prevented from flowing through the vent conduit valve means. The vent conduit valve means is responsive to a signal to assume one of the positions.

In an embodiment, the control means sends a supply signal to the first supply device to effect a stop state of the first supply device. The control device further sends one or more signals to the at least one valve means to effect a closed position of the first exit valve means and the second inlet conduit valve means and an open position for the second exit conduit valve means and the vent conduit valve means for discharging fluid from the chamber.

Preferably, the embodiments further comprise at least one fitting disposed between an opening and its associated conduit means for retaining the conduit means in the opening at high pressure. The fitting forms a fluid-tight seal between the opening and associated conduit means and retains the associated conduit means in the opening when the pressure in the chamber is elevated. Preferably, the fitting retains he conduit means in the opening at a chamber pressure between 15,000 and 120,000 psi.

In one embodiment, the chamber has a cylindrical wall, a first end wall and a second end wall. In this embodiment, the first inlet opening is positioned in either the first or second end wall and the first exit opening is positioned in the other end wall. The second inlet opening is positioned through the cylindrical wall proximate the first exit opening and the second exit opening is positioned through the cylindrical wall proximate the first inlet opening. When there is a vent opening, the vent opening is positioned through the cylindrical wall approximately diametrically opposite the second input opening.

The housing enclosing the chamber is comprised of an inert material, which may be stainless steel, titanium or other metals that are inert to the fluids being used.

A method for injecting one or more fluids into an exit conduit at high pressure utilizes a device comprising a housing with a number of openings, conduits in the openings, and at least one valve means to control flow in the conduits. The method comprises providing a housing that has a chamber for receiving and/or holding one or more fluids under pressure and an exterior surface. The housing has at least a first exit opening, a first inlet opening, a second exit opening, and a second inlet opening. Each opening extends from the chamber to the exterior surface. Each opening can receive a conduit.

A first exit conduit means is received by the first exit opening. The first exit conduit means is in communication with the chamber for transporting fluids from the chamber out of the first exit opening. The first exit conduit means is used for connection with an analytical device, such as a HPLC column. Preferably the first exit conduit means is a capillary. The first inlet opening receives a first inlet conduit means. The first inlet conduit means is in communication the chamber for transporting a first fluid into the chamber. The first inlet conduit means is used for connection to a first supply device, such as a pump.

The second inlet opening receives the second inlet conduit means. The second inlet conduit means is in communication with the chamber for transporting a second fluid into the chamber. The second inlet conduit means is used for connection with a second supply device, such as a reservoir or pump. Preferably, the first fluid is a solute and the second fluid is a sample fluid The second exit conduit means is received by the second exit opening. The second exit conduit means is in communication with the chamber for transporting fluids from the chamber out of the second exit opening. The second exit conduit means is used for connection with a waste receptacle or recycling means.

At least one valve means is disposed in at least one of the first exit conduit means, the second exit conduit means and the second inlet conduit means. Each of the at least one valve means is operable with a pressure differential across the valve means of between 15,000 and 120,000 psi. The valve means has a closed position wherein fluid is prevented from flowing through the valve means and an open position wherein the fluid is allowed to flow through the valve means. The valve means is responsive to a signal to assume one of the positions. Preferably the valve means are freeze-thaw valves.

The method comprises receiving a fluid from each of the first inlet conduit means and the second inlet conduit means, and discharging fluid through the first exit conduit means and the second exit conduit means.

Preferably, the method involves further providing a first supply device, a source of a second fluid and a control means. The first supply device is connected to the first inlet conduit means. The first supply device has a supply state wherein the first fluid is supplied at a pressure up to a maximum pressure and a stop state wherein the first fluid is not supplied. The first supply device is responsive to a supply signal to assume one of the states. The first supply device may be a pump. The source of the second fluid is in fluid communication with the second inlet conduit means. The control means is for controlling each of the at least one valve means by sending a signal to the valve means to assume one of the open and closed positions and for controlling the first supply device by sending a supply signal to the first supply device to assume one of the supply and stop states.

The method comprises causing the control means to send one or more signals to the valve means and the first supply device to effect a sequence of positions and states for moving one or more fluids through the first exit conduit means. To inject a quantity of the first fluid into the exit conduit means, the control means performs the actions of: a. sending a signal to all the conduit valve means to effect a closed state for sealing the chamber, b. sending a supply signal to the first supply device to effect a supply state for providing the first fluid and for raising the pressure of the first fluid to an impelling pressure in the chamber, and c. sending a signal to the first exit conduit valve means to effect an open position for injecting a quantity of the first fluid into the first exit conduit means.

To remove first fluid from the chamber and inject the second fluid into the exit conduit means, the control means starts by reducing the pressure in the chamber. The control means performs the actions of sending a signal to the first exit conduit valve means to effect a closed position, sending a supply signal to the first supply device to effect a stop state and sending a signal to the second exit conduit valve means to effect an open position. Then, when the pressure in the chamber reaches ambient pressure, the control means sends a signal to the second inlet conduit valve means to effect an open position. The control means allows the second fluid to feed into the chamber until the second fluid has displaced the first fluid. Then, the control means brings the pressure in the chamber to the impelling pressure by sending a signal to the second inlet conduit valve means and the second exit conduit valve means to effect a closed position, and sending a supply signal to the first supply device to effect a supply state. While maintaining the pressure in the chamber at the impelling pressure, the control means sends a signal to the first exit conduit valve means to effect an open position for a predetermined period of time to inject the second fluid onto the first exit conduit means.

When the device further comprises a fluid monitor that monitors a fluid passing through the second exit conduit, the monitor provides the control means information about the composition of the fluid exiting the chamber. Using the fluid monitor information, the control means saves second fluid by feeding the second fluid into the chamber only until the information from the fluid monitor indicates that the second fluid has displaced the first fluid. This conserves second fluid over a method that flows second fluid for a period of time sufficient to assure that the first fluid has been displaced.

To reduce pressure in the chamber and discharge fluid from the chamber, the control means sends a signal to the first exit conduit valve means to effect a closed position and sends a signal to the second exit conduit valve means to effect an open position. When the device further comprises a vent opening in the housing, a vent conduit means and a vent conduit valve means, the control means also sends a signal to the vent conduit valve means to effect an open position. This allows fluid to discharge from the chamber more quickly. The vent opening extends from the chamber to the exterior surface for receiving the vent conduit means. The vent conduit means is received by the vent opening and is in communication with the chamber for transporting fluids from the chamber out of the vent opening. The vent conduit means is for connection with a waste collection means. The vent conduit valve means is interposed in the vent conduit means. The vent conduit valve means is of the type previously described with an open and closed position. The valve means is responsive to a signal to assume one of the positions.

With the device incorporating a vent opening, vent conduit means and vent conduit valve means, the control means may execute a different sequence to remove first fluid from the housing and inject the second fluid into the exit conduit means. The control means starts by reducing the pressure in the housing by performing the actions of sending a signal to the first exit conduit valve means to effect a closed position, sending a supply signal to the first supply device to effect a stop state and sending a signal to the second exit conduit valve means and vent conduit valve means to effect an open position. Then, when the pressure in the housing reaches a ambient pressure, the control means sends a signal to the vent conduit valve means to effect a closed position and to the second inlet conduit valve means to effect an open position.

The control means allows second fluid to feed into the chamber until the second fluid has displaced the first fluid. Then the control means brings the pressure in the chamber to the impelling pressure by sending a signal to the second inlet conduit valve means and the second exit conduit valve means to effect a closed position, and sending a supply signal to the first supply device to effect a supply state. Once the pressure in the chamber is at the impelling pressure, the control means sends a signal to the first exit conduit valve means to effect an open position for a predetermined time to inject the second fluid onto the capillary.

With the device incorporating a vent opening, vent conduit means and vent conduit valve means, to reduce the pressure in the housing and discharge the second fluid from the chamber, the control means sends a signal to the first exit conduit valve means to effect a closed position and sends a signal to the second exit conduit valve means and the vent conduit valve means to effect an open position.

Other systems, methods, features and advantages of the present invention will be or become apparent to one skilled in the art upon examination of the following drawings and detailed description. It is intended that all such additional systems, methods, features and advantages be included within this description, be within the scope of the present invention, and be protected by the accompanying claims.

DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numbers designate corresponding parts throughout the several views.

DETAILED DESCRIPTION

The present invention is generally related to liquid chromatography and, more particularly is directed to a device for impelling one or more fluids through a high pressure liquid chromatography (HPLC) column. The HPLC column is connected to a conduit that exits from the device. The device comprises a housing with a number of openings, conduits in the openings, and at least one valve means to control flow in the conduits.

Figure 1:
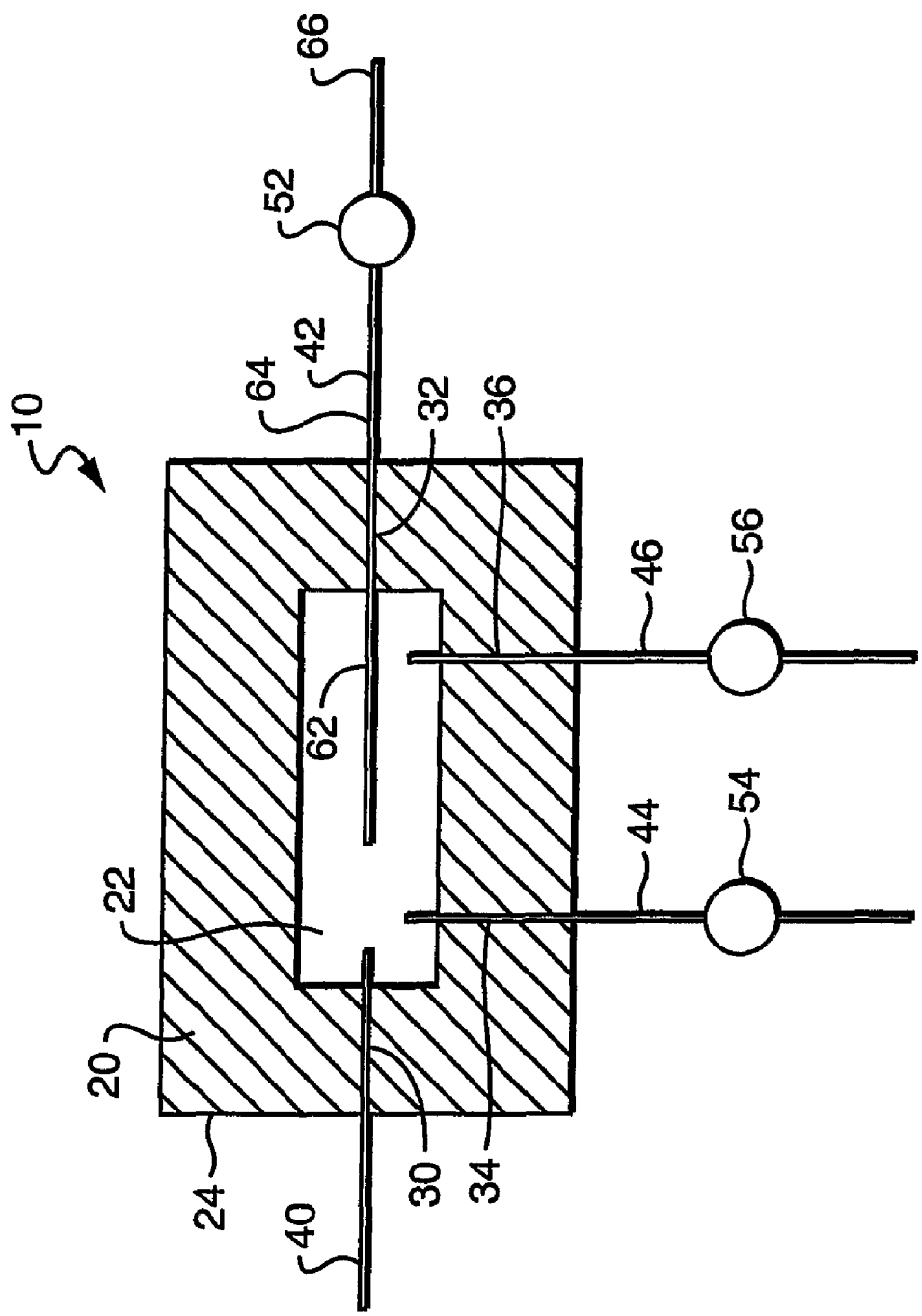
FIG. 1 is a representation of an embodiment of the inventive device.

The device 10, as schematically illustrated in FIG. 1, comprises a housing 20 that has a chamber 22 for receiving and/or holding one or more fluids under pressure and an exterior surface 24. The housing 20 has at least a first exit opening 32, a first inlet opening 30, a second exit opening 34, and a second inlet opening 36. Each opening extends from the chamber 22 to the exterior surface 24. Each opening is configured to receive a conduit means.

A first exit conduit means 42 is received by the first exit opening 32. The first exit conduit means 42 is in communication with the chamber 22 for transporting fluids from the chamber 22 out of the first exit opening 32. The first exit conduit means 42 is used for connection with an analytical device, such as a HPLC column (not shown). The first inlet opening 30 receives the first inlet conduit means 40. The first inlet conduit means 40 is in communication with the chamber 22 for transporting a first fluid into the chamber 22. The first inlet conduit means has an inner diameter of between approximately 120 µm and 180 µm. The first inlet conduit means 40 is used for connection to a first supply device (not shown), such as a pump.

The second inlet opening 36 receives the second inlet conduit means 46. The second inlet conduit means 46 is in communication with the chamber 22 for transporting a second fluid into the chamber. The second inlet conduit means 46 is used for connection with a second supply device (not shown), such as a reservoir or pump. The second exit conduit means 44 is received by the second exit opening 34. The second exit conduit means 44 is in communication with the chamber 22 for transporting fluids from the chamber 22 out of the second exit opening 34. The second exit conduit means 44 is used for connection with a waste receptacle or recycling means (not shown).

The chamber 22 is adapted for receiving fluid from the first inlet conduit means 40 and the second inlet conduit means 46, and for discharging fluid through the first exit conduit means 42 and the second exit conduit means 44. Preferably the first fluid is a solute while the second fluid is sample fluid. The chamber 22 is further adapted to hold a fluid at a high, very high and/or ultra high pressure.

At least one valve means is disposed in at least one of the first exit conduit means 42, the second exit conduit means 44 and the second inlet conduit means 46. Each of the valve means is operable with a pressure differential across the valve means of between approximately 15,000 to 120,000 psi. The valve means has a closed position wherein fluid is prevented from flowing through the valve means and an open position wherein the fluid is allowed to flow through the valve means. The valve means is responsive to a signal to assume one of the positions. In a preferred embodiment, the at least one valve means is a freeze-thaw valve. Such valves have no moving parts and contribute no dead volume to the separation, allowing reproducible operation in an in-line environment. The freeze-thaw valve means are used to control loading and pressurization of the device.

Figure 2:
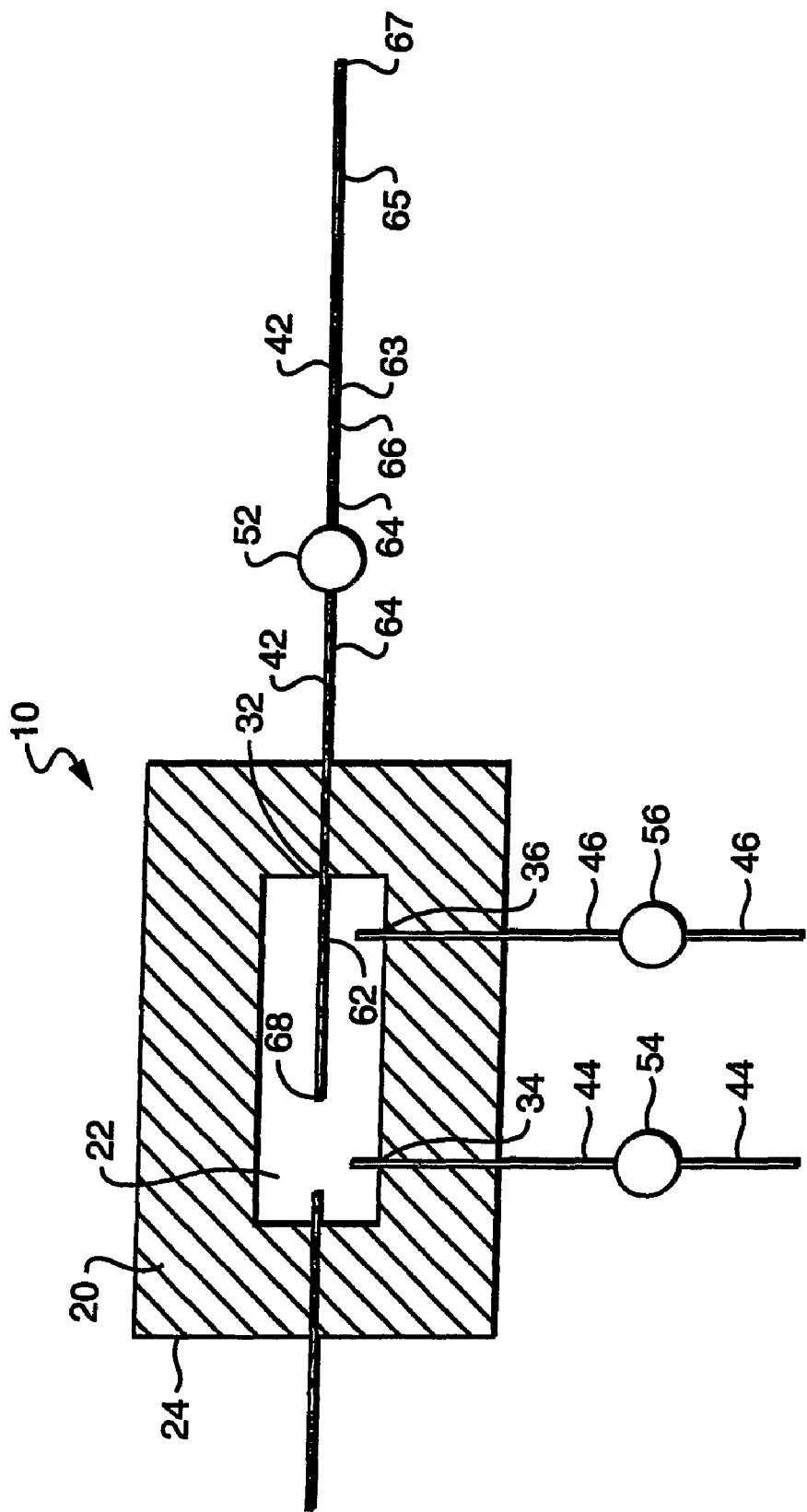
FIG. 2 is a representation of the device of FIG. 1 illustrating a column connected to the device.

Turning now to FIG. 2, a first exit conduit valve means 52 is interposed in the first exit conduit means 42. As illustrated, the first exit conduit means 42 is a capillary having a first end 62 through the first exit opening 32, a mid-portion 64 external to the housing 20, and a second end 66 formed as a liquid chromatography column 65 having an input end 63 and an output end 67. The first exit conduit means 42 and the column 65 have an inner diameter between approximately 15 µm and 150 µm. The first exit conduit valve means 52 is disposed in the mid-portion 64 of the first exit conduit means 42. As illustrated, the first end 62 of the first exit conduit means 42 extends into the chamber 22 with the tip 68 of the first end 62 of the first exit conduit means 42 positioned in the chamber 22 between the second inlet opening 36 and the second exit opening 34. This positioning assures that when the second fluid flows in the second inlet opening 36 and out the second exit opening 34, the area around the tip 68 of the first exit conduit means 42 will be swept and any first fluid in the chamber will not be retained near the first exit conduit means 42.

Figure 3:
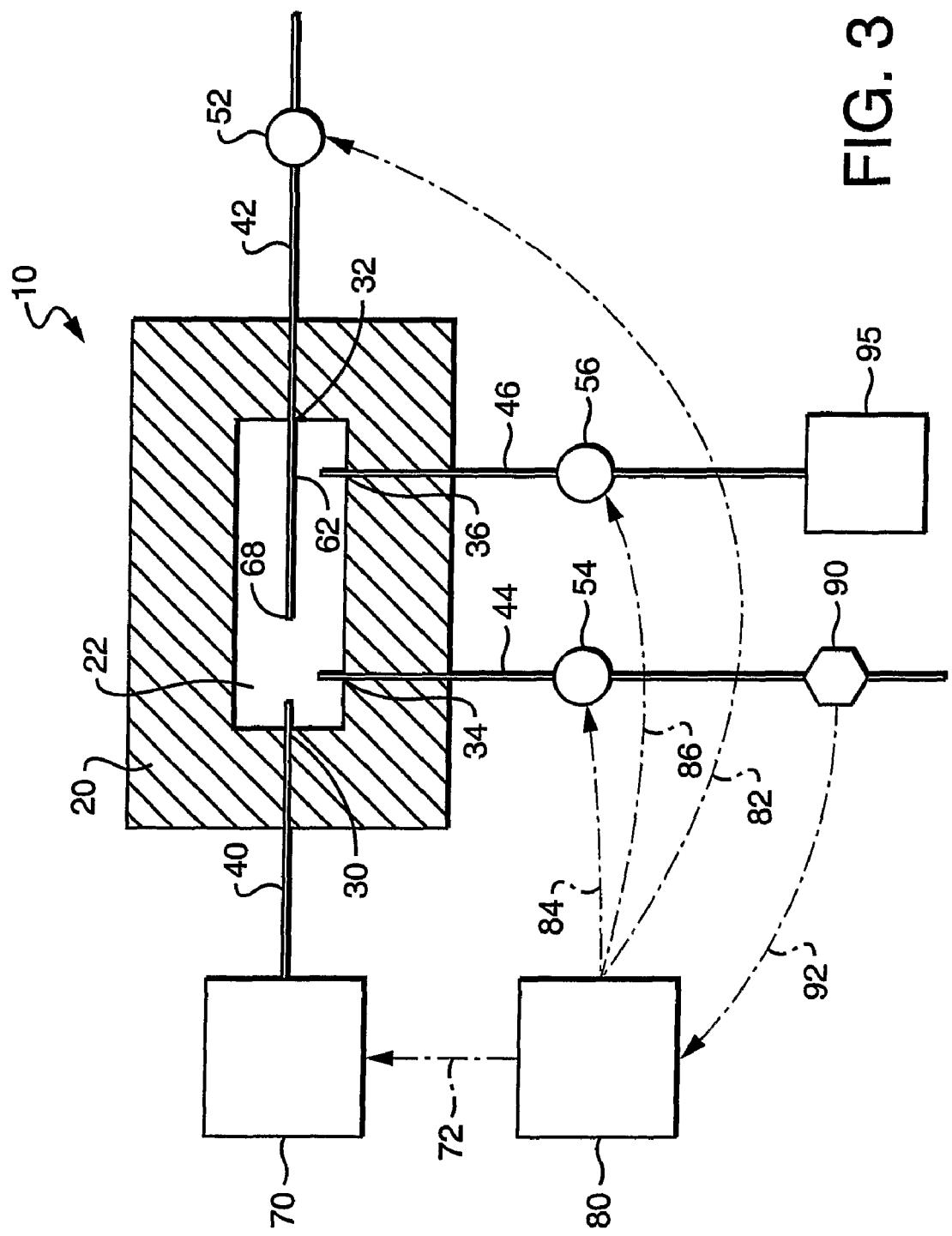
FIG. 3 is a representation of the device of FIG. 1 illustrating status and control signal connections.

As illustrated in FIG. 3, a second exit conduit valve means 54 is interposed in the second exit conduit means 44. Preferably a second inlet conduit valve means 56 is interposed in the second inlet conduit means 46. A second fluid source 95 is connected to the second inlet conduit 46 for supplying the second fluid. The second inlet and second exit openings accommodate a conduit means 46, 44 having an inner diameter between approximately 15 μm and 50 μm.

The device 10 is illustrated connected to a first supply device 70 by the first inlet conduit means 40. The first supply device 70 has a supply state wherein the first fluid is supplied at a pressure up to a maximum pressure. The first supply device 70 also has a stop state wherein the first fluid is not supplied. The first supply device 70 is responsive to a supply signal 72 to assume one of the states.

As illustrated, the device 10 also comprises a control means 80 for controlling each of the at least one valve means by sending a signal 82, 84, 86 to the valve means to assume one of the open and closed positions. As illustrated, the control means 80 further controls the first supply device 70 by sending a supply signal 72 to the supply device 70 to assume one of the supply and stop states.

To fill and pressurize the chamber 22, the control means 80 sends a supply signal 72 to the first supply device 70 to effect a supply state of the first supply device 70. The control means 80 further sends one or more signals to the at least one valve means to effect a closed position of all conduit valve means 52, 54, 56 for filling and pressurizing the chamber 22.

To replace existing fluid in the chamber 22 with the second fluid, the control means 80 sends a supply signal 72 to the first supply device 70 to effect a stop state of the first supply device 70 and sends one or more signals to the at least one valve means to effect a closed position of the first exit conduit valve means 52 and an open position of the second inlet conduit valve means 56 and the second exit conduit means 54 for replacing a fluid in the chamber 22 with the second fluid. Preferably, as illustrated, the device 10 comprises a fluid monitor 90 for monitoring a fluid passing through the second exit conduit means 44. The fluid monitor is for providing the control means 80 with a monitor signal 92 indicative of the composition of the fluid exiting the chamber 22. Preferably, the control means 80 monitors the fluid at the second exit conduit 44 through said monitor signal 92 and determines the concentration of the second fluid in the discharge fluid.

To discharge fluid from chamber 22, the control means 80 sends a supply signal 72 to the first supply device 70 to effect a stop state of the first supply device 70 and sends one or more signals to the at least one valve means to effect a closed position of the first exit valve means 52 and the second inlet valve means 56 and an open position of the second exit valve means 54 for discharging fluid from the chamber 22.

To impel a pressurized fluid through the first exit conduit means 42, the control means 80 sends a supply signal 72 to the first supply device 70 to effect a supply state of the first supply device 70 and sends one or more signals to the at least one valve means to effect a closed position of the second inlet valve means 56 and the second exit valve means 54 and an open position of the first exit valve means 52 for impelling the pressurized fluid through the first exit conduit means 42.

In one embodiment, the first supply device 70 is a pump able to raise the pressure internal to the chamber 22 to the maximum pressure. The maximum pressure is preferably between 15,000 and 120,000 psi. The pump can be a binary pump capable of generating a gradient at the maximum pressure. When the chamber is filled with second fluid at the time the pump is turned to the supply state, the pump raises the pressure and compresses the existing fluid. However the first fluid does not necessarily displace the second fluid unless fluid exits the chamber.

In one embodiment, the chamber 22 is designed and constructed to hold fluids at pressures between approximately atmosphere and the maximum pressure. In one embodiment, the maximum pressure extends up to approximately 5000 psi. In another embodiment the maximum pressure extends up to approximately 15,000 psi. In a third embodiment the maximum pressure extends up to approximately 120,000 psi and in particular, the pressure in the chamber is between approximately 30,000 psi and 120,000 psi when fluid is impelled through the first exit opening 32.

Figure 4:
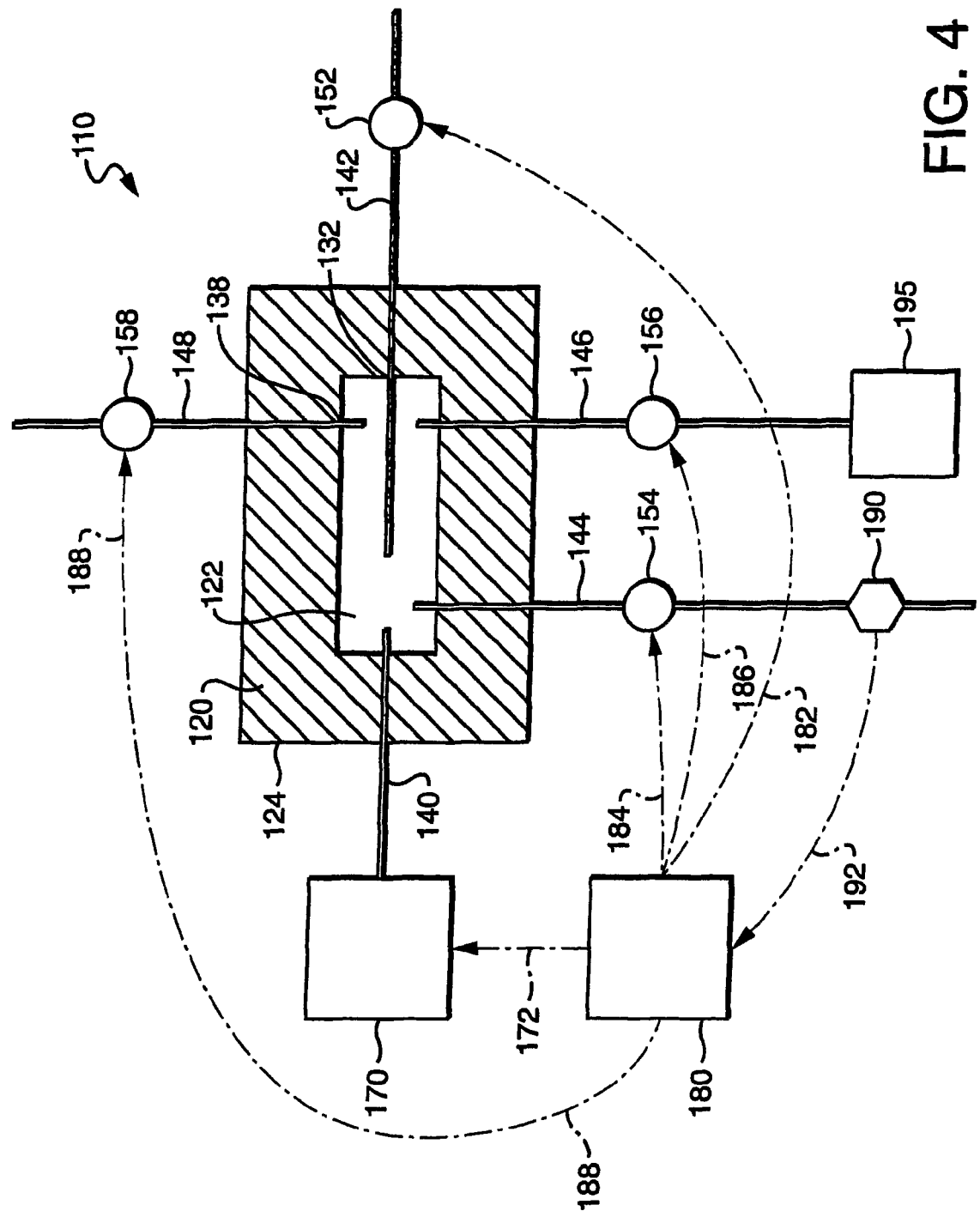
FIG. 4 is a representation of a different embodiment of the inventive device.

The device 110, as shown in FIG. 4, is illustrated further comprising a vent opening 138 in the housing 120 extending from the chamber 122 to the exterior surface 124 for receiving a vent conduit means 148. The vent conduit means 148 that is received by the vent opening 138 is in communication with the chamber 122 for transporting fluids from the chamber 122 out of the vent opening 138. One vent conduit means 148 has an inner diameter between approximately 25 μm and 150 μm. As illustrated, the vent conduit means 148 has a vent conduit valve means 158 disposed within it. The vent conduit valve means 158 interposed in the vent conduit means 148 has an open position wherein fluid is allowed to flow through the vent conduit valve means 158 and a closed position wherein fluid is prevented from flowing through the vent conduit valve means 158. The vent conduit valve means 158 is responsive to signal 188 to assume one of the positions.

In general, the inner diameters of the second inlet conduit means 146 and second exit conduit means 144 are the smallest diameters used with the device 110. The first exit conduit means 142 is the next largest and the vent conduit means 148 and first inlet conduit means 140 are the largest of the conduit means used with the device 110. This hierarchy allows for maximum control of the amount of second fluid utilized and control of the fluids impelled onto the column (not shown) while minimizing the time spent depleting pressure in the chamber 122 between process steps.

To discharge fluid from the chamber 122, the device of FIG. 4 has the control means 180 send a supply signal 172 to the first supply device 170 to effect a stop state of the first supply device 170. The control means 180 further sends one or more signals to the at least one valve means to effect a closed position of the first exit valve means 152 and the second inlet conduit valve means 156 and an open position for the second exit conduit valve means 154 and the vent conduit valve means 158 for discharging fluid from the chamber 122. The device 110 dissipates the pressure more quickly and discharges fluids from the chamber 122 more quickly due to the larger diameter of the vent conduit means 148 and the ability to open both the vent conduit valve means 158 and the second conduit exit valve means 154 simultaneously.

Figure 5:
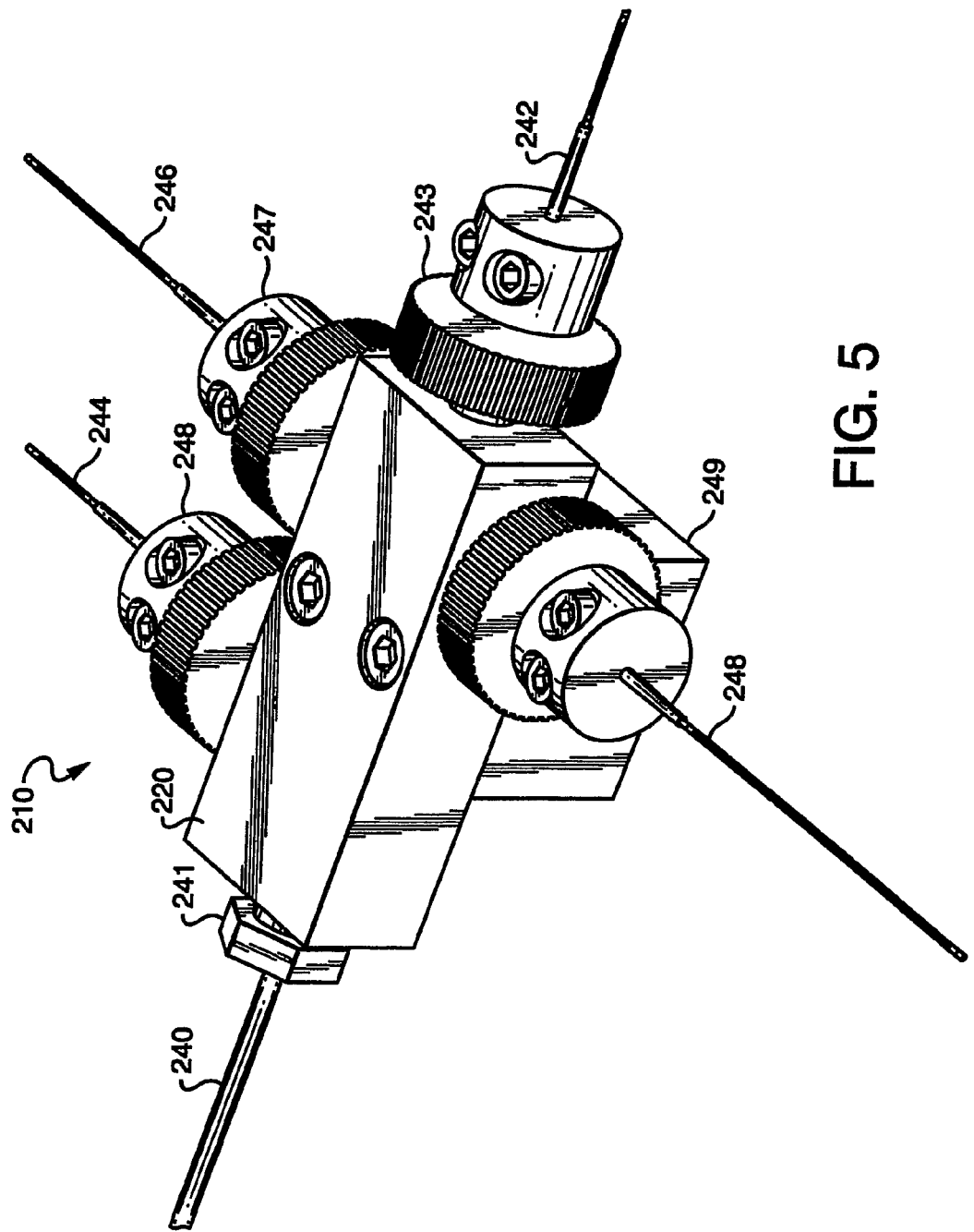
FIG. 5 is a perspective drawing of the device of FIG. 5.

In implementing the device, for instance device 210, as shown in FIG. 5, the embodiments may further comprise at least one fitting, such as fitting 243, disposed between an opening and its associated conduit means. Such a fitting is described in co-pending application 60/410,346 the content of which is expressly incorporated herein by reference in its entirety. This fitting 243 is for forming a fluid-tight seal between the opening and associated conduit means, especially when the conduit means is formed of fused silica. Fused silica is too fragile to withstand the forces that would be applied by a standard high-pressure ferrule such as ferrule 241. The fitting 243 is also for retaining the associated conduit means in the opening when the pressure in the chamber is elevated. The fitting 243 retains the conduit means in the opening up to a chamber pressure between approximately 15,000 and 120,000 psi. When the conduit means is formed of a metallic material, such as stainless steel, titanium, or other inert metal, as illustrated by the first inlet conduit means 240, a simpler high pressure fitting such as fitting 241 may be used. This fitting 241 may be a high-pressure ferrule. The housing 220 comprises an inert material, which may be stainless steel, titanium or other metal inert to the fluids being used, that is able to withstand the maximum pressure.

The housing is disposed about a chamber that is preferably between 1 and 3 cm long and has a diameter of between 35 and 60 mm. Such dimensions allow small quantities of sample and solute to be used. One chamber utilized was approximately 1.7 cm long with a diameter of approximately 45 mm. The housing 220 to enclose such a chamber has dimension that are preferably between 1 and 2 inches long, 0.5 to 1.0 inches wide and 0.35 to 0.7 in high. One housing implemented was 1.5 in×0.7 in×0.4 in.

In one implementation, the housing 220 described above was manufactured as shown in FIG. 6A with an internal cylindrical chamber 222 that was approximately 0.65 in long and had a diameter of about 0.018 in, therefore having a volume of 0.306 in$^3$. The housing 220 was manufactured of stainless steel. Chamber 222 had a sidewall 223 about the chamber 222 and had open ends. A first inlet opening 230 was connected to the first end 225 of the chamber 222. The first inlet opening 230 was constructed to receive a Waters Corp. (Milford Ma) Z-detail stainless ferrule fitting. A second exit opening 234 was provided in the sidewall 233 of the chamber 222 with the center of the second exit opening 234 approximately 0.017 in along the sidewall 233 from the first end 235 of the chamber 222. The second exit opening 234 was placed very close to the first end 235 of the chamber 222 to minimize any residual first fluid when the second fluid was replacing the first fluid. The second end opening 234 was constructed to receive a #6-40 ferrule as detailed in FIG. 6C. The first exit opening 232 was provided as shown in detail in FIG. 6B connected to the open second end 227 of the chamber 222. The second inlet opening 236 and the vent opening 238 were provided on either side of the chamber 222 through the sidewall 233 at approximately 0.035 in in from the second end 227 of the chamber 222. Each of the first exit opening 232, second inlet opening 236, and vent opening 238 were constructed to receive a 6-40 ferrule as illustrated in FIG. 6C.

Figure 6A:
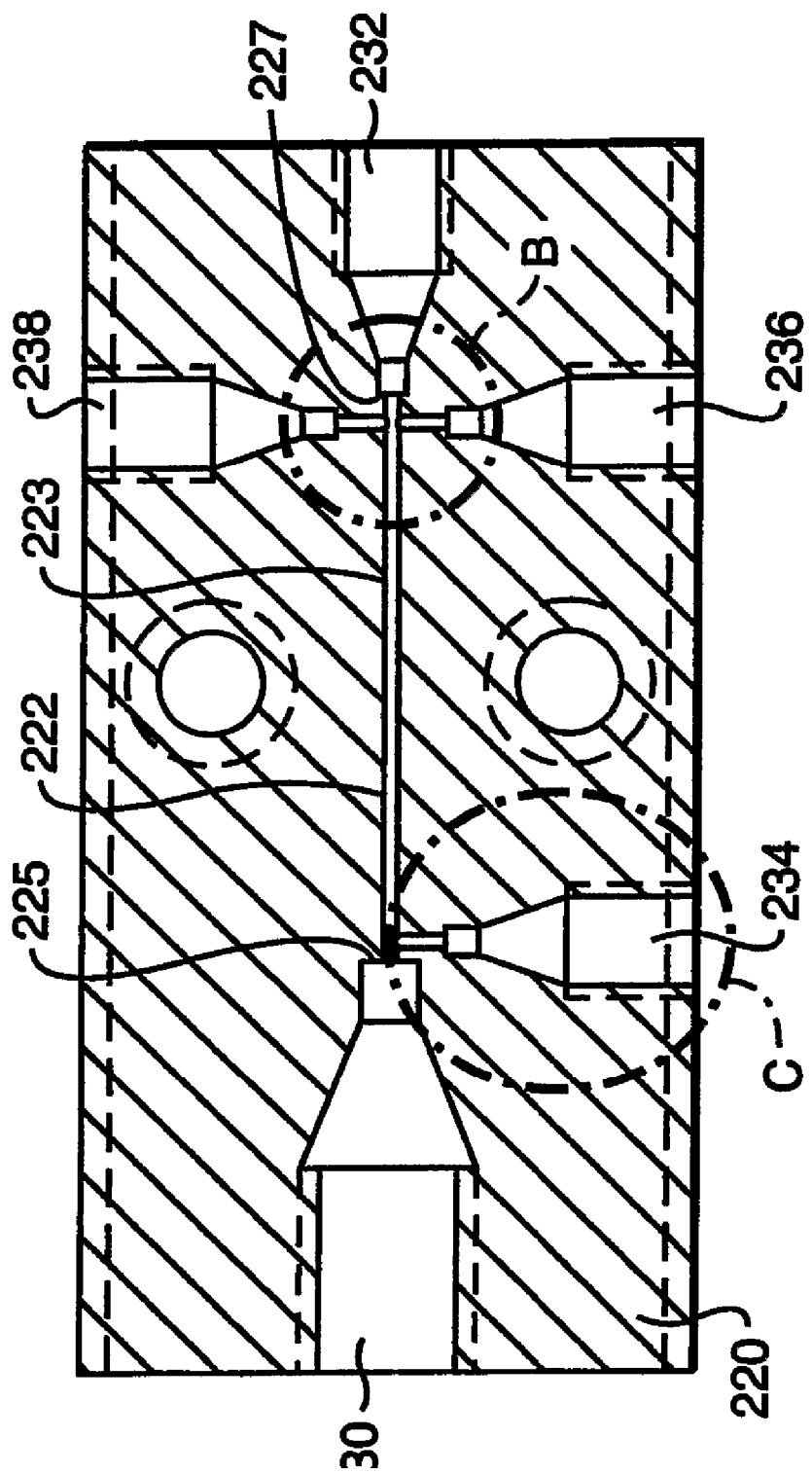
FIG. 6A is a top view of the housing of an embodiment of the device of FIG. 5.
Figure 6B:
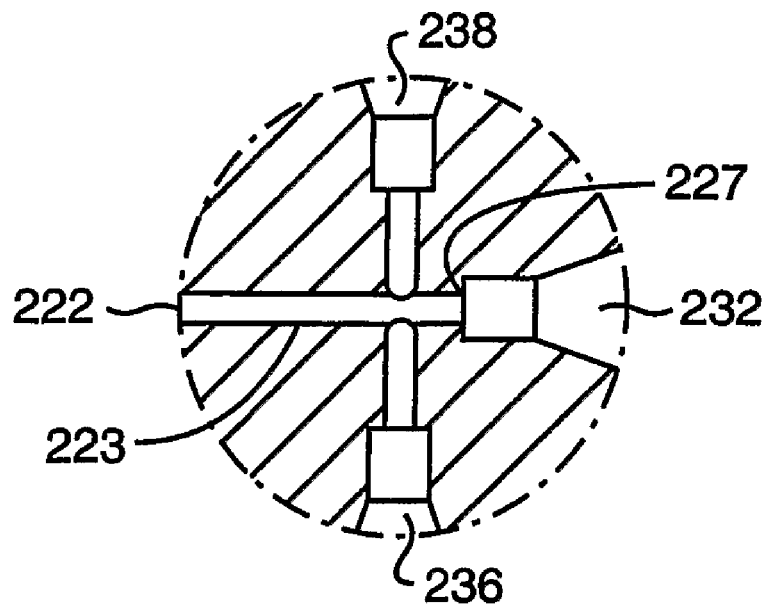
FIG. 6B is a detail of an opening in the housing of FIG. 6A
Figure 6C:
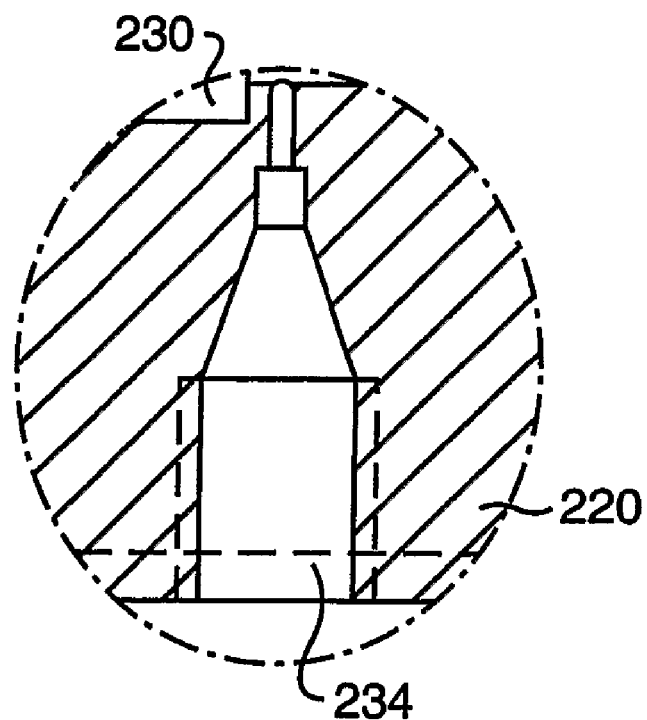
FIG. 6C is a detail of a feature of the housing of FIG. 6A.
Figure 7A:
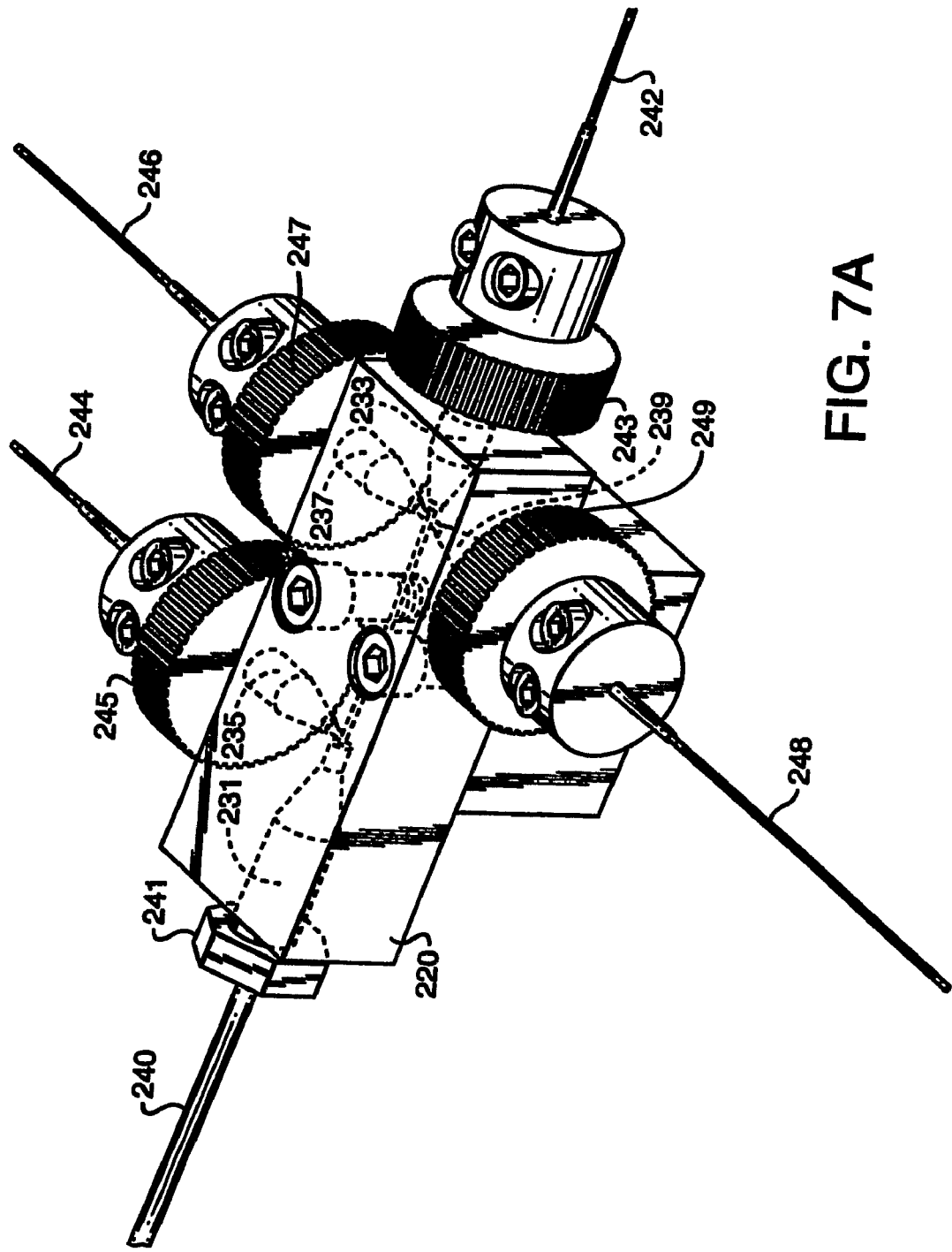
FIG. 7A is a perspective drawing of the device of FIG. 5 with the housing of FIG. 6A illustrated as transparent to show interconnection details of the embodiment.

In one embodiment, illustrated in FIG. 7A wherein the housing 220 of FIG. 6A is rendered as transparent to reveal the chamber 222, the device is built up from the housing as illustrated. The first inlet opening 230 is fit with a ferrule 231 to retain a first inlet conduit means 240 in the opening. The first inlet conduit means 240 has an inner diameter that is the largest of the conduit means to allow efficient pressure build up and flushing of the chamber. The first inlet conduit means 240 has an inner diameter of preferably between 120 and 180 μm and an outer diameter of approximately 360 μm. In one instance the first inlet conduit means had an inner diameter of 150 μm and outer diameter of 360 μm. The first inlet conduit means 240 is preferably made of stainless steel and retained by a compression fitting 241 such as the Waters Z-detail as used on a Waters Alliance HPLC system (Waters Corp, Milford Mass.). Alternately, a fused silica capillary of the same size range can be used for the first inlet conduit means 240. The retention mechanism for the fused silica conduit means would be a high-pressure capillary fitting, as described above, adapted to interface with ferrule 231 to retain the fused silica capillary without damaging the capillary.

The first exit opening 232 is fit with a ferrule 233 to retain a first exit conduit means 242 in the opening. The first exit conduit means 242 has an inner diameter that is no larger than the inner diameter of the first inlet conduit means 240 and is adapted to the chromatographic process to be carried out. Typically the first exit conduit means 242 has an inner diameter of between 15 and 150 μm and an outer diameter of approximately 360 μm. In one instance, the first exit conduit means 242 had an inner diameter of 70 μm and, external to the housing 220, was packed with media particles forming a column external to the housing. A high-pressure capillary fitting 243, adapted to interface with the ferrule 233, retains the fused silica capillary in the first exit opening 232 without damaging the capillary.

The second inlet opening 236 is positioned proximate the first exit opening 232. The second inlet opening 236 is fit with a ferrule 237 to retain the second inlet conduit means 246 in the opening. The second inlet conduit means 246 has an inner diameter of between 15-50 μm and an outer diameter of approximately 360 μm. In one instance, the second inlet conduit means 246 had an inner diameter of 25 μcm. A high-pressure capillary fitting 247, adapted to interface with the ferrule 237, retains the fused silica capillary in the second inlet opening 236 without damaging the capillary.

The second exit opening 234 is positioned proximate the first inlet opening 230. The second exit opening 234 is fit with a ferrule 235 to retain the second exit conduit means 244 in the opening. The second exit conduit means 244 has an inner diameter of between 15-50 μm and an outer diameter of approximately 360 μm. In one instance, the second exit conduit means 244 had an inner diameter of 25 μm. A high-pressure capillary fitting 245, adapted to interface with the ferrule 235, retains the fused silica capillary in the second exit opening 234 without damaging the capillary.

When there is a vent opening, the vent opening 238 is positioned approximately diametrically opposite the second input opening 236. The vent opening 238 is fit with a ferrule 239 to retain the vent conduit means 248 in the opening. The vent conduit means 248 has an inner diameter of between 25-150 μm and an outer diameter of approximately 360 μm. In one instance, the vent conduit means 248 had an inner diameter of 50 μm. A high-pressure capillary fitting 249, adapted to interface with the ferrule 239, retains the fused silica capillary in the vent opening 238 without damaging the capillary. Valve means (not shown) are disposed around the first exit conduit means, second inlet conduit means, second exit conduit means and vent conduit means external to the housing.

Figure 7B:
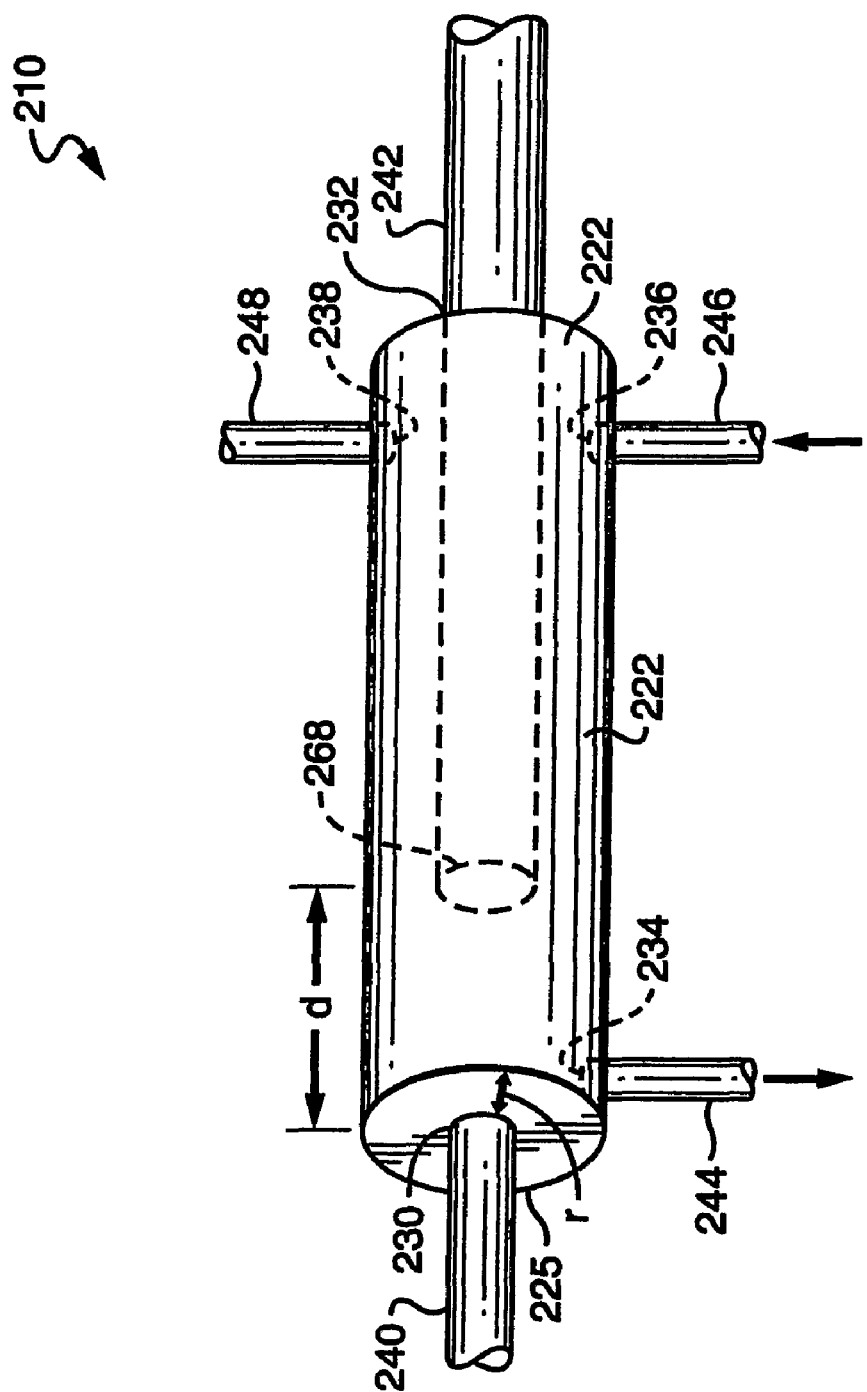
FIG. 7B is a representation of the internals of the chamber of the device of FIG. 7A.

FIG. 7B illustrates how the quantity of second fluid that to be impressed into the first exit conduit means 242 is controlled by the placement of the tip 268 of the first exit conduit means 242. The first exit conduit means 242 is inserted into the chamber 222 through the first exit opening 232. The tip 268 of the first exit conduit means 242 is disposed between the second inlet opening 236 and the second exit opening 234 a distance 'd' from end wall 225. When the chamber 222 is filled with second fluid, by flowing second fluid in through the second inlet conduit means 246 and out the second exit conduit means 244, the volume between the tip 268 of the first exit conduit means 242 and the end wall 225 is filled with second fluid. This volume of second fluid is determined by:

$$V = d\pi r^2$$

where "r" is the radius of the chamber. After the chamber 222 is sealed, this volume of second fluid remains between the tip 268 and the end of the chamber 225. When the pump connected to the first inlet conduit means 240 is placed into a supply state, the pump tries to inject first fluid into the chamber 222. However, because the chamber 222 is filled with second fluid, the pump only raises the pressure on the second fluid. When the pressure is sufficiently high, the first exit conduit valve means (not shown) is opened and a quantity of second fluid is impelled into the first exit conduit means 242 while an equal quantity of first fluid replaces the second fluid. This quantity of first fluid is contained against the end of the chamber 225. The device 210 can impel second fluid into the end 268 of the first exit conduit means 242 only until all the second fluid in the volume determined by the equation above is moved. Thereafter, the first fluid that is being provided by the first supply device will be impelled onto the conduit means. While the volume of fluid calculated above is an upper limit on the quantity of second fluid that may be injected, the duration of time that the first exit valve means is open while the chamber 222 is pressurized typically determines the quantity of second fluid injected.

In one embodiment using the interconnections of FIG. 4 to the device of FIGS. 6 and 7, the first input conduit 240, a steel 150μ ID×1/16" OD conduit, was connected, by a metallic ferrule fitting (Waters Corp Z detail ferrule), between the first inlet opening 230 and an ultra-high pressure binary gradient pump acting as the first supply device 170. The first exit conduit 242, a 75 μ ID×360μ OD fused silica capillary, was held in the first exit opening 232 by a high-pressure capillary fitting that mated with the 6-40 ferrule opening. The second inlet and exit conduits 246, 244, 25μ ID×360μ OD capillary, were held in each of the second inlet and second exit openings 236, 234 by a high-pressure capillary fitting that mated with the 6-40 ferrule opening. The vent conduit 248, a 25μ ID×360μ OD capillary, was held in the vent opening 238 by a high-pressure capillary fitting that mated with the 6-40 ferrule opening. The first exit conduit 242 was fed through the high-pressure fitting until it was positioned with the end of the conduit approximately 500 μm away from the first end 235 of the chamber 222.

The device with the conduit held in place was mounted in an enclosure. Freeze-thaw valve assemblies were positioned about the first exit conduit 242, the second input 246 and exit conduit 244 and the vent conduit 248 respectively. In one implementation, one freeze-thaw valve was positioned around both the second inlet conduit 246 and the second exit conduit 244 controlling the flow in these conduits simultaneously. With this implementation, the second inlet conduit 246 and second exit conduit 244 were used exclusively for filling the chamber with second fluid. The vent conduit 248 was used for depressurization and discharging of pressurized fluid from the chamber 222.

A method for injecting one or more fluids into an exit conduit at high pressure utilizes a device, such as that illustrated in FIG. 3. The device comprises a housing 30 with a number of openings, conduits in the openings, and the at least one valve means to control flow in the conduits as described above. The first exit conduit means 42, in the first exit opening 32, is used for connection with an analytical device, such as a HPLC column. The first exit conduit means 42 may be a capillary. The first inlet conduit means 40, in the first inlet opening 30, is in communication with the chamber 22 for transporting a first fluid into the chamber 22. The first inlet conduit means 40 is used for connection to a first supply device 70, such as a pump that supplies a first fluid such as a solute.

The second inlet conduit means 46, in the second inlet opening 36, is in communication with the chamber 22 for transporting a second fluid into the chamber 22. The second inlet conduit means 46 is used for connection with a second supply device 95, such as a reservoir or pump that supplies a second fluid such as a sample. The second exit conduit means 44, in the second exit opening 34, is in communication with the chamber 22 for transporting fluids from the chamber 22. The second exit conduit means 44 is used for connection with a waste receptacle or recycling means.

At least one valve means is disposed in at least one of the first exit conduit means 42, the second exit conduit means 44 and the second inlet conduit means 46. Each of the at least one valve means is operable with a pressure differential across the valve means of up to 120,000 psi. The valve means has a closed position wherein fluid is prevented from flowing through the valve means and an open position wherein the fluid is allowed to flow through the valve means. The valve means is responsive to a signal to assume one of the positions. Preferably the valves are freeze-thaw valves. The chamber 22 receives fluid from each of the first inlet conduit means 40 and the second inlet conduit means 46, and discharges fluid through the first exit conduit means 42 and the second exit conduit means 44.

In addition to the above device, a further method utilizes a first supply device 70, a source of a second fluid 95 and a control means 80. The first supply device 70 is connected to the first inlet conduit means 40. The first supply device 70 has a supply state wherein the first fluid is supplied at a pressure up to a maximum pressure and a stop state wherein the first fluid is not supplied. The first supply device 70 is responsive to a supply signal 72 to assume the supply state or the stop state. The first supply device 70 may be a pump, a binary pump, or a gradient pump. The source of the second fluid 95 is in fluid communication with the second inlet conduit means 46. The control means 80 is for controlling each of the at least one valve means by sending a signal 82, 84, 86 to the valve means 52, 54, 56 to assume one of the open and closed positions. The control means is also for controlling the first supply device 70 by sending a supply signal 72 to the first supply device 70 to assume one of the supply and stop states.

The method comprises causing the control means 70 to send one or more signals to the valve means and the first supply device 70 to effect a sequence of positions and states for moving one or more fluids through the exit conduit means 42, 44. To inject a quantity of first fluid into the exit conduit means 42, the control means 70 performs the actions of: a. sending a signal to all the conduit valve means to effect a closed state for sealing the chamber 22, b. sending a supply signal 72 to the first supply device 70 to effect a supply state for providing the first fluid and for raising the pressure of the first fluid to an impelling pressure in the chamber 22, and c. sending a signal 82 to the first exit conduit valve means 52 to effect an open position for injecting a quantity of the first fluid into the first exit conduit means 42.

To remove first fluid from the chamber 22 and inject second fluid into the exit conduit means 42, the control means 80 starts by reducing the pressure in the chamber 22. The control means 80 performs the actions of sending a signal 82 to the first exit conduit valve means 52 to effect a closed position, sending a supply signal 72 to the first supply device 70 to effect a stop state and sending a signal 84 to the second exit conduit valve 54 means to effect an open position. Then, when the pressure in the chamber 22 reaches ambient pressure, the control 80 means sends a signal 86 to the second inlet conduit valve 56 means to effect an open position. The control means 80 allows second fluid to feed into the chamber 22 until the second fluid has displaced the first fluid. Then, the control means 80 brings the pressure in the chamber 22 to the impelling pressure by sending a signal 86, 84 to the second inlet conduit valve means 56 and the second exit conduit valve means 54 to effect a closed position, and sending a supply signal 72 to the first supply device 70 to effect a supply state. While maintaining the pressure in the chamber 22 at the impelling pressure, the control means 80 sends a signal 82 to the first exit conduit valve means 52 to effect an open position for a predetermined time to inject the second fluid onto the first exit conduit means 42.

When the device 10 further comprises a fluid monitor 90 that monitors a fluid passing through the second exit conduit means 44, the fluid monitor 90 provides the control means 80 information about the composition of the fluid exiting the chamber. 22 via a monitor signal 92. Using the fluid information in the monitor signal 92, the control means 80 can save second fluid during the replacement operation by feeding the second fluid into the chamber 22 only until the information on the monitor signal 92 indicates that the second fluid has displaced the first fluid.

To reduce the pressure in chamber 22 and discharge fluid from chamber 22, the control means 80 sends a signal 82 to the first exit conduit valve means 52 to effect a closed position and sends a signal 84 to the second exit conduit valve means 54 to effect an open position. As shown in FIG. 4, when device 110 further comprises a vent opening 138 in the housing 120, a vent conduit means 148 and a vent conduit valve means 158, the control means 180 effects a discharge by sending a signal 188 to the vent conduit valve 158 means to effect an open position. This allows fluid to discharge from the chamber 122 more quickly. The vent opening 138 extends from the chamber 122 to the exterior surface 124 for receiving the vent conduit means 148. The vent conduit means 148 is received by the vent opening 138 and is in communication with the chamber 122 for transporting fluids from the chamber 122 out of the vent opening 138. The vent conduit valve means 158 is interposed in the vent conduit means 148. The vent conduit valve means 158 is of the type previously described having an open and closed position. The vent conduit valve means 158 is responsive to signal 188 to assume one of the positions.

With the device 110 incorporating a vent opening 138, vent conduit means 148 and vent valve means 158, the control means 180 removes first fluid from the chamber 122 and injects the second fluid into the exit conduit means 142 using a different sequence of operations. The control means 180 reduces the pressure in the chamber 122 by performing the actions of sending a signal 182 to the first exit conduit valve means 152 to effect a closed position, sending a supply signal 172 to the first supply device 170 to effect a stop state and sending a signal 184, 188 to the second exit conduit valve means 154 and vent conduit valve means 158 to effect an open position. Alternately, when the vent conduit means 148 has a significantly larger diameter than the second exit conduit means 144, the vent conduit valve means 158 alone can be placed in the open position to reduce the pressure. When the pressure in the chamber 122 reaches ambient pressure, the control means 180 sends a signal 188 to the vent conduit valve means 158 to effect a closed position and signals 184, 186 to the second exit conduit valve means 154 and the second inlet conduit valve means 156 to effect an open position. The control means 180 allows second fluid to feed into the chamber 122 until the second fluid has displaced the first fluid. Then the control means 180 brings the pressure in the chamber 122 to the impelling pressure by sending a signal 186,184 to the second inlet conduit valve means 156 and the second exit conduit valve 154 means to effect a closed position, and sending a supply signal 172 to the first supply device 70 to effect a supply state. Once the pressure in the chamber 122 is at the impelling pressure, the control means 180 sends a signal 182 to the first exit conduit valve means 152 to effect an open position for a predetermined time to inject the second fluid onto the exit conduit means 142.

To reduce the pressure in the chamber 122 and discharge the second fluid from the chamber 122, from the device 110 incorporating a vent opening 138, vent conduit means 148 and vent valve means 158, the control means 180 sends a signal 182 to the first exit conduit valve means 152 to effect a closed position and sends a signal 184 to the second exit conduit valve means 154 and the vent conduit valve means 158 to effect an open position.

Those skilled in the art will recognize, or be able to ascertain using no more than routine experimentation, numerous equivalents to the specific procedures, embodiments, claims and examples described herein. Such equivalents were considered to be within the scope of this invention and covered by the claims appended hereto. The contents of all references, issued patents, and published patent applications cited throughout this application are hereby incorporated by reference.

Example

A method embodying features of the present inventive device will now be described with respect to the following example.

A 75 µm ID by 20 cm long column, packed with 1 µm C18 (Waters Corp., Milford Mass.) particles was placed in fluid communication with a 75 µm ID capillary. The capillary was threaded through the first exit conduit freeze-thaw valve 252 and then through the first exit high-pressure capillary fitting installed in the first exit conduit opening. The capillary was inserted into the opening until the tip of the capillary was approximately 500 µm away from the first end 235 of the chamber 222. The capillary was then secured in position by tightening the high-pressure capillary fitting.

The column was first flushed with a 95% water/5% ACN solution by applying 30 kpsi from the pump through the chamber 222 with the first exit valve 252 in the open position and all other valves in the closed position for 10 min. The first exit valve 252 was then placed in a closed position and the vent valve 258 was placed in the open position to bring the pressure to ambient. The vent valve 258 was then placed in the closed position and the second inlet and exit valves 256, 254 were placed in the open position. The sample, an 8 uM BSA digest, flowed from the second inlet conduit means 246 to the second exit conduit means 244, replacing the solute until the output of a monitor on the output of the second output conduit means 244 indicated that the chamber 222 was filled with sample. The second inlet and exit valves 256, 254 were placed in a closed position, and the pump was started to place 10 kpsi on the sample in the chamber 222. The first exit valve 252 was placed in the open position and sample was injected onto the column for 0.7 min. at 10 kpsi placing approximately 1 fmol of sample on the column. The first exit valve 252 was placed in the closed position and the vent valve 258 was placed in the open position to remove the sample from the chamber 222. The vent valve 258 was placed in the closed position, and the pump was further activated to pressurize the fluid in the chamber 222 to 30 kpsi. The pump then executed a 20 minute gradient (5%A->95% B), A=5% ACN, B=70% ACN, each with 0.1% formic acid. The output of the column was analyzed using a Waters Micromass Q-TOF mass spectrometer (Waters Corp., Milford Mass.) yielding a separation with narrow Gaussian-shaped peptide peaks, illustrating that a well-characterized sample band had been injected onto the column.

The injector device as described can be used in an automated manner to sequence samples and then solute through one column without manual intervention. The device as described can be used in applications ranging from high pressure injections through ultra high pressure injections. The device shows better reproducibility than separations conducted in separate loading and separation devices. This improvement can be attributed to the better control of the amount of sample injected.

One skilled in the art will appreciate further features and advantages of the invention based on the above-described embodiments. Accordingly, the invention is not to be limited by what has been particularly shown and described, except as indicated by the appended claims.

What is claimed is:

1. A device for impelling one or more liquids through an exit conduit comprising:
   a housing having a chamber for receiving and/or holding one or more liquids under pressure and an exterior surface, and said housing having at least a first exit opening, a first inlet opening, a second exit opening, and a second inlet opening, each opening extending from said chamber to said exterior surface for receiving conduit means;
   a first exit conduit means received by said first exit opening in communication with said chamber for transporting liquids from said chamber out of said first exit opening, said first exit conduit means for connection with an analytical device;
   a first inlet conduit means received by said first inlet opening in communication said chamber for transporting a first liquid into said chamber, said first inlet conduit means for connection to a first supply device;
   a second inlet conduit means received by said second inlet opening in communication with said chamber for transporting a second liquid into said chamber, said second inlet means for connection with a second supply device;
   a second exit conduit means received by said second exit opening in communication with said chamber for transporting liquids from said chamber out of said second exit opening, said second exit conduit means for connection with a waste receptacle;
   at least one valve means disposed in at least one of said first exit conduit means, said second exit conduit means and said second inlet conduit means, said valve means having a closed position wherein liquid is prevented from flowing through said valve means and an open position wherein said liquid is allowed to flow through said valve means, said valve means responsive to a signal to assume one of said positions; and
   at least one fitting disposed between an opening and its associated conduit means, for forming a liquid-tight seal between said opening and associated conduit means and for retaining said associated conduit means in said opening when said pressure in said chamber is elevated,
   wherein said chamber is for receiving liquid from each of said first inlet conduit means and said second inlet conduit means, and for discharging liquid through said first exit conduit means and said second exit conduit means, and
   wherein said at least one fitting retains the associated conduit means in the opening at a chamber pressure between 15,000 psi and a maximum pressure of 120,000 psi.

2. The device of claim 1 wherein said at least one valve means is a freeze-thaw valve.

3. The device of claim 2 wherein said first liquid is a solute.

4. The device of claim 2 wherein said second liquid is a sample liquid.

5. The device of claim 1 further comprising a first exit conduit valve means interposed in said first exit conduit means.

6. The device of claim 5 wherein said first exit conduit means is a capillary having a first end in said first exit opening, a mid portion external to said housing, and a second end formed as a liquid chromatography column having an input end and an output end, wherein said first exit conduit valve means is disposed in said mid portion.

7. The device of claim 6 wherein said first end of said capillary extends into said chamber.

8. The device of claim 7 wherein a tip of said first end of said capillary is positioned in said chamber between said second inlet opening and said second exit opening.

9. The device of claim 6 wherein said capillary has an inner diameter between approximately 15 µm and 150 µm.

10. The device of claim 1 further comprising a first supply device connected to said first inlet conduit means, said first supply device having a supply state wherein said first liquid is supplied at a pressure up to said maximum pressure and a stop state wherein said first liquid is not supplied, said first supply device responsive to a supply signal to assume one of said states.

11. The device of claim 10 further comprising a control means for controlling each of said at least one valve means by sending a signal to said valve means to assume one of said open and closed positions.

12. The device of claim 11 further comprising a control means for controlling a first supply device by sending a supply signal to said supply device to assume one of said supply and stop states.

13. The device of claim 12 wherein said control means sends a supply signal to said first supply device to effect a supply state of the first supply device and sends one or more signals to said at least one valve means to effect a closed position of all conduit valve means for filling and pressurizing said chamber.

14. The device of claim 12 wherein said control means sends a supply signal to said first supply device to effect a stop state of said first supply device and sends one or more signals to said at least one valve means to effect a closed position of said first exit conduit valve means and an open position of said second inlet conduit valve means and said second exit conduit means for replacing a liquid in said chamber with said second liquid.

15. The device of claim 12 further comprising a liquid monitor for monitoring a liquid passing through said second exit conduit means for providing said control means with information about the composition of the liquid exiting said chamber.

16. The device of claim 15 wherein said control means monitors said liquid at said second exit conduit for determining concentration.

17. The device of claim 12 wherein said control means sends a supply signal to said first supply device to effect a stop state of said first supply device and sends one or more signals to said at least one valve means to effect a closed position of said first exit valve means and said second inlet valve means and an open position of said second exit valve means for discharging liquid from said chamber.

18. The device of claim 12 wherein said control means sends a supply signal to said first supply device to effect a supply state of said first supply device and sends one or more signals to said at least one valve means to effect a closed position of said second inlet valve means and said second exit valve means and an open position of said first exit valve means for impelling a pressurized liquid through said first exit conduit means.

19. The device of claim 10 wherein said first supply device is a pump able to supply liquid against a pressure internal to said chamber up to said maximum pressure.

20. The device of claim 19 wherein said pump is a binary pump capable of generating a gradient at said maximum pressure.

21. The device of claim 19 wherein said chamber is designed and constructed to hold liquids at pressures between approximately atmosphere and said maximum pressure.

22. The device of claim 21 wherein said pressure in said chamber is between approximately 30,000 psi and 100,000 psi when liquid is impelled through said first exit opening.

23. The device of claim 1 further comprising a second exit conduit valve means interposed in said second exit conduit means.

24. The device of claim 1 further comprising a second inlet conduit valve means interposed in said second inlet conduit means.

25. The device of claim 1 further comprising a second liquid source connected to said second inlet conduit valve for supplying said second liquid.

26. The device of claim 1 further comprising:
a vent opening in said housing extending from said chamber to said exterior surface for receiving a vent conduit means; and a vent conduit means received by said vent opening in communication with said chamber for transporting liquids from said chamber out of said vent opening, said vent conduit means for connection with a vent conduit valve means.

27. The device of claim 26 further comprising a vent conduit valve means interposed in said vent conduit means having an open position wherein liquid is allowed to flow through said vent conduit valve means and a closed position wherein liquid is prevented from flowing through said vent conduit valve means, and wherein said vent conduit valve means is responsive to a signal to assume one of said positions.

28. The device of claim 27 wherein said control means sends a supply signal to said first supply device to effect a stop state of said first supply device and sends one or more signals to said at least one valve means to effect a closed position of said first exit valve means and said second inlet conduit valve means and an open position for said second exit conduit valve means and said vent conduit valve means for discharging liquid from said chamber.

29. The device of claim 26 wherein said vent conduit means has an inner diameter between approximately 25 μm and 150 μm.

30. The device of claim 26 wherein said chamber has a cylindrical wall, a first end wall and a second end wall.

31. The device of claim 30 wherein said first inlet opening is positioned in one of the walls selected from said first and second end walls and said first exit opening is positioned in the other wall selected from said first and second end walls.

32. The device of claim 31 wherein said second inlet opening is positioned through said cylindrical wall proximate said first exit opening and said second exit opening is positioned through said cylindrical wall proximate said first inlet opening.

33. The device of claim 32 wherein said vent opening is positioned through said cylindrical wall approximately diametrically opposite said second input opening.

34. The device of claim 1 wherein said housing comprises an inert material.

35. The device of claim 34 wherein said inert material is stainless steel or titanium.

36. The device of claim 1 wherein said second inlet and second exit openings accommodate a conduit means having an inner diameter between approximately 15 μm and 50 μm.

37. A method for injecting one or more liquids into an exit conduit at high pressure comprising:
providing a housing having a chamber for receiving and/or holding one or more liquids under pressure and an exterior surface, and said housing having at least a first exit opening, a first inlet opening, a second exit opening, and a second inlet opening, each opening extending from said chamber to said exterior surface for receiving conduit means;
providing a first exit conduit means received by said first exit opening in communication with said chamber for transporting liquids from said chamber out of said first exit opening, said first exit conduit means for connection with an analytical device;
providing a first inlet conduit means received by said first inlet opening in communication said chamber for transporting a first liquid into said chamber, said first inlet conduit means for connection to a first supply device;
providing a second inlet conduit means received by said second inlet opening in communication with said chamber for transporting a second liquid into said chamber, said second inlet means for connection with a second supply device;
providing a second exit conduit means received by said second exit opening in communication with said chamber for transporting liquids from said chamber out of said second exit opening, said second exit conduit means for connection with a waste receptacle;
providing at least one valve means disposed in at least one of said first exit conduit means, said second exit conduit means and said second inlet conduit means, said valve means having a closed position wherein liquid is prevented from flowing through said valve means and an open position wherein said liquid is allowed to flow through said valve means, said valve means responsive to a signal to assume one of said open position and said closed position;
providing at least one fitting disposed between an opening and its associated conduit means, for forming a liquid-tight seal between said opening and associated conduit means and for retaining said associated conduit means in said opening when said pressure in said chamber is elevated; and
receiving a liquid from each of said first inlet conduit means and said second inlet conduit means; and discharging liquid through said first exit conduit means and said second exit conduit means,
wherein said at least one fitting retains the associated conduit means in the opening at a chamber pressure between 15,000 psi and a maximum pressure of 120,000 psi.

38. The method of claim 37 further comprising providing a first supply device connected to said first inlet conduit means, said first supply device having a supply state wherein said first liquid is supplied at a pressure up to a maximum pressure and a stop state wherein said first liquid is not supplied, said first supply device responsive to a supply signal to assume one of said states.

39. The method of claim 38 further comprising providing a source of said second liquid in liquid communication with said second inlet conduit means.

40. The method of claim 39 further comprising providing a control means for controlling each of said at least one valve means by sending a signal to said valve means to assume one of said open and closed positions and for controlling a first supply device by sending a supply signal to said first supply device to assume one of said supply and stop states.

41. The method of claim 40 further comprising causing said control means to send one or more signals to said valve means and said first supply device to effect a sequence of positions and states for moving one or more liquids through said exit conduit means.

42. The method of claim 41 wherein said control means injects a quantity of said first liquid into said first exit conduit means by performing the actions comprising: a. sending a signal to all said conduit valve means to effect a closed state for sealing said chamber; b. sending a supply signal to said first supply device to effect a supply state for providing said first liquid and for raising a pressure of said first liquid to an impelling pressure in said chamber; and c. sending a signal to said first exit conduit valve means to effect an open position for injecting a quantity of said first liquid into said first exit conduit means.

43. The method of claim 41 wherein said control means injects said second liquid into said first exit conduit means by performing the actions comprising: a. sending a signal to said first exit conduit valve means to effect a closed position, sending a supply signal to said first supply device to effect a stop state and sending a signal to said second exit conduit valve means to effect an open position, for reducing pressure in said chamber; b. when pressure in said chamber reaches a ambient pressure, sending a signal to said second inlet conduit valve means to effect an open position; c. feeding said second liquid into said chamber until said second liquid has displaced said first liquid; d. sending a signal to said second inlet conduit valve means and said second exit conduit valve means to effect a closed position, and sending a supply signal to said first supply device to effect a supply state to bring said pressure in said chamber to an impelling pressure; and e. maintaining said pressure in said chamber at said impelling pressure and sending a signal to said first exit conduit valve means to effect an open position for a predetermined time to inject said second liquid onto said first exit conduit means.

44. The method of claim 43 wherein said device further comprises a liquid monitor that monitors a liquid passing through said second exit conduit means for providing said control means information about the composition of said liquid exiting said chamber.

45. The method of claim 44 wherein step c is replaced by: feeding said second liquid into said chamber until said information from said liquid monitor indicates said second liquid has displaced said first liquid.

46. The method of claim 41 wherein said control means performs the actions comprising sending a signal to said first exit conduit valve means to effect a closed position and sending a signal to said second exit conduit valve means to effect an open position to reduce said pressure in said chamber and flush liquid from said chamber.

47. The method of claim 39 wherein said first liquid is a solute and said second liquid is a sample liquid.

48. The method of claim 38 wherein said first supply device is a pump.

49. The method of claim 37 wherein said first exit conduit means is a capillary.

50. The method of claim 41 wherein said device further comprises: a vent opening in said housing extending from said chamber to said exterior surface for receiving a vent conduit means; a vent conduit means received by said vent opening in communication with said chamber for transporting liquids from said chamber out of said vent opening; said vent conduit means for connection with a vent conduit valve means ; and a vent conduit valve means interposed in said vent conduit means, said valve means having a closed position wherein liquid is prevented from flowing through said valve means and an open position wherein said liquid is allowed to flow through said valve means, said valve means responsive to a signal to assume one of said positions.

51. The method of claim 50 wherein said control means injects a quantity of said first liquid into said first exit conduit means by performing the actions comprising: a. sending a signal to all said conduit valve means to effect a closed state for sealing said chamber; b. sending a supply signal to said first supply device to effect a supply state for providing said first liquid and for raising a pressure of said first liquid to an impelling pressure in said housing; and c. sending a signal to said first exit conduit valve means to effect an open position for injecting a quantity of said first liquid into said first exit conduit means.

52. The method of claim 50 wherein said control means injects said second liquid into said first exit conduit means by performing the actions comprising: a. sending a signal to said first exit conduit valve means to effect a closed position, sending a supply signal to said first supply device to effect a stop state and sending a signal to said second exit conduit valve means and said vent conduit valve means to effect an open position, for reducing pressure in said housing; b. when pressure in said housing reaches a ambient pressure, sending a signal to said vent conduit valve means to effect a closed state and to said second inlet conduit valve means to effect an open position; c. feeding said second liquid into said chamber until said second liquid has displaced said first liquid; d. sending a signal to said second inlet conduit valve means and said second exit conduit valve means to effect a closed position, and sending a supply signal to said first supply device to effect a supply state to bring said pressure in said chamber to said impelling pressure; and e. maintaining said pressure in said chamber at said impelling pressure and sending a signal to said first exit conduit valve means to effect an open position for a predetermined time to inject said second liquid onto said first exit conduit means.

53. The method of claim 50 wherein said control means performs the actions comprising sending a signal to said first exit conduit valve means to effect a closed position and sending a signal to said second exit conduit valve means and said vent conduit valve means to effect an open position to reduce said pressure in said housing and flush said second liquid from said chamber.

54. The method of claim 37 wherein said valves are freeze-thaw valves.

* * * * *